United States Patent [19]

Goldschmitt et al.

[11] 4,382,039

[45] May 3, 1983

[54] PROCESS FOR THE PREPARATION OF 4-NITROTOLUENE-2-SULPHONIC ACID

[75] Inventors: Ernst Goldschmitt, Cologne; Peter Schnegg; Heinz U. Blank, both of Odenthal, Fed. Rep. of Germany

[73] Assignee: Bayer Aktiengesellschaft, Leverkusen, Fed. Rep. of Germany

[21] Appl. No.: 370,216

[22] Filed: Apr. 20, 1982

Related U.S. Application Data

[63] Continuation of Ser. No. 139,496, Apr. 11, 1980, abandoned.

[30] Foreign Application Priority Data

Apr. 26, 1979 [DE] Fed. Rep. of Germany ....... 2916912

[51] Int. Cl.³ .......................................... C07C 143/24
[52] U.S. Cl. .............................................. 260/505 R
[58] Field of Search ...................... 260/505 R, 505 E

[56] References Cited

FOREIGN PATENT DOCUMENTS 2419455 11/1974 Fed. Rep. of Germany ...... 260/505

OTHER PUBLICATIONS

Gilbert, "Sulfonation & Related Reactions" (1965) pp. 71, 82.

*Primary Examiner*—Alan Siegel
*Attorney, Agent, or Firm*—Sprung, Horn, Kramer & Woods

[57] ABSTRACT

In a process for the preparation of 4-nitrotoluene-2-sulphonic acid by reacting 4-nitrotoluene with gaseous sulphur trioxide at an elevated temperature, the improvement wherein molten 4-nitrotoluene is reacted with gaseous sulphur trioxide at a temperature in the range from 60° to 150° C. under a pressure above the vapor pressure of 4-nitrotoluene, in a molar ratio of sulphur trioxide to 4-nitrotoluene of 0.1:1 to 1.5:1, and, after a conversion of at least 70 percent of the reaction component not employed in excess is achieved, the sulphonation mixture is treated with water.

11 Claims, No Drawings

PROCESS FOR THE PREPARATION OF 4-NITROTOLUENE-2-SULPHONIC ACID

This is a continuation, of application Ser. No. 139,496, filed Apr. 11, 1980 now abandoned.

The invention relates to a process for the preparation of 4-nitrotoluene-2-sulphonic acid by reacting molten 4-nitrotoluene with gaseous sulphur trioxide.

It is known (German Offenlegungsschrift No. 2,419,455) to prepare p-nitrotoluene-2-sulphonic acid by reacting molten p-nitrotoluene with a mixture of at most 50% by volume of gaseous sulphur trioxide and an inert gas at a temperature of 90° to 150° C.

In this procedure, the reaction mixture is obtained as a black, tarry suspension towards the end of the addition of sulphur trioxide and, after hydrolysis of the p-nitrotoluene-2-sulphonic acid anhydride with water, an aqueous solution of p-nitrotoluene-2-sulphonic acid is formed from the suspension, and this is treated with active charcoal, before or after separating off water-insoluble by-products, in order to separate off dissolved, coloured compounds and dissolved, unreacted p-nitrotoluene.

The procedure described in German Offenlegungsschrift No. 2,419,455 has the disadvantage that it is carried out with sulphur trioxide diluted by an inert gas. Hence considerable technical effort is required to purify the inert gas beforehand, for example to dry the inert gas, or afterwards, for example to separate off volatile p-nitrotoluene and/or sulphur trioxide entrained in the stream of inert gas. Moreover, in this procedure a special device is required to conduct the stream of inert gas out of the reaction vessel. In spite of this considerable technical effort, a yield of p-nitrotoluene-2-sulphonic acid of only about 95% is achieved and the product contains tarry impurities.

Furthermore, German Offenlegungsschrift No. 2,353,918 and German Offenlegungsschrift No. 2,354,097 disclose a process for the preparation of aromatic sulphonic acids by treatment of aromatic hydrocarbons with gaseous $SO_3$, in which the reaction takes place under a continuously maintained large excess of aromatic hydrocarbon, as the heat transfer medium, under reflux conditions. According to German Offenlegungsschrift No. 2,354,097, an inert compound which dissolves the aromatic substance and the sulphonic acid formed therefrom is employed as the heat transfer medium. The reaction temperature, which can be regulated via the pressure, is between 20° and 100° C. and corresponds to the reflux temperature.

Physical factors in the case of the sulphonation of p-nitrotoluene (boiling point: 105° C./9 mm Hg) mean that the solvent-free process can be carried out on an industrial scale by the procedure indicated above only with considerable effort. Even the proposed use of solvents means an additional technical effort, if any organic solvents which are sufficiently stable towards $SO_3$ at all are available in the temperature range in question.

A process has now been found for the preparation of 4-nitrotoluene-2-sulphonic acid by reacting 4-nitrotoluene with gaseous sulphur trioxide at elevated temperature, which is characterised in that molten 4-nitrotoluene is reacted with gaseous sulphur trioxide at temperatures in the range from about 60° to about 150° C. under pressures above the vapour pressure of 4-nitrotoluene, in a molar ratio of $SO_3$ to 4-nitrotoluene of 0.1:1 to 1.5:1, and, after a conversion of at least about 70% of the reaction component not employed in excess is achieved, the sulphonation mixture is treated with water.

The reaction mixture thereby obtained can be subjected to further purification.

In the process according to the invention, after a conversion of at least about 70% of the reaction component not employed in excess, the sulphonation mixture is treated with water in an amount such that, after hydrolysis of the sulphonic acid anhydrides present in the mixture at about 80° to 100° C. in the course of about 0.01 sec to 600 minutes, especially 1 to 60 minutes and particularly preferred 30 to 60 minutes, a 4-nitrotoluene-2-sulphonic acid solution of a concentration suitable for further processing, for example about 20 to 70% strength by weight, is formed and can be purified by adsorption or extraction. The solution is preferably extracted, if appropriate after filtering off the sparingly soluble sulphone, with an organic solvent which is not miscible with water in all proportions. After separating off the residual amounts of the solvent used for the extraction, a pure approximately 40% strength solution of 4-nitrotoluene-2-sulphonic acid of excellent quality is obtained, as can be seen from the following data:

Sum of all the organic impurities: 1 ppm
Colour number of a 40% strength solution: 4 to 6
(Gardner Colour Standard; compare German Offenlegungsschrift 2,419,455).

The water added to the reaction mixture after a conversion of at least about 70% of the reaction component not employed in excess has been achieved can also be employed in the form of aqueous alkali metal hydroxide solutions and/or of acid, neutral or alkaline aqueous solutions, which have, or, preferably, have not been prepurified, which already contain dissolved 4-nitrotoluenesulphonic acid in an amount such that, together with the 4-nitrotoluenesulphonic acid from the sulphonation mixture, a concentration of 4-nitrotoluenesulphonic acid of about 20 to 70% by weight is established.

The yield of 4-nitrotoluene-2-sulphonic acid is about 98 to 99.5% of theory (relative to reacted 4-nitrotoluene).

The above result is the more surprising since it had to be assumed from the state of the art that 4-nitrotoluene can be reacted with sulphur trioxide to give a product of satisfactory quality in good yield only by the application of special measures, such as inert gas dilution, reflux conditions, use of solvents or diluents or a large excess of aromatic hydrocarbons to be sulphonated.

As described above, reaction temperatures in the range from about 60° to 150° C. are suitable for the sulphonation, and those of from 80° to 130° C., and especially from 90° to 125° C., are advantageous. The particularly preferred temperature range is from 100° to 120° C.

The process according to the invention can be carried out under a slight increased pressure, under decreased pressure or under normal pressure.

The process according to the invention is advantageously carried out under pressures above the vapour pressure of 4-nitrotoluene, preferably under normal pressure.

If sulphur trioxide is passed in the form of a gas into the reaction mixture, a certain increased pressure may be necessary, in which case care must be taken that no condensation of the sulphur trioxide take place.

The process according to the invention can be carried out by mixing gaseous $SO_3$ intensively with molten 4-nitrotoluene in a molar ratio of about 0.1:1 to 1.5:1, preferably 0.7:1 to 1.3:1 and particularly preferably 0.9:1 to 1.2:1, in a temperature range from about 80° to 130° C., the reaction temperature chosen being maintained during the mixing operation by cooling. Some minutes after the mixing operation, at the latest after about 10 hours, a conversion of the reaction component, not employed in excess, of at least 70% of theory has been achieved under the reaction conditions. The conversion of the component not employed in excess is preferably about 85%, and particularly preferably more than 90%, of theory.

When the desired conversion has been achieved, 100 to 500 ml of water, for example, per mol of 4-nitrotoluene employed are added to the reaction mixture and the mixture is stirred, in general for up to about 60 minutes, at an elevated temperature of about 80° to 100° C. An approximately 20 to 70% strength, pale yellow to reddish crude solution of 4-nitrotoluene-2-sulphonic acid is obtained, in which the unreacted 4-nitrotoluene is dissolved or emulsified and small amounts of crystalline sulphone may be suspended. The yield of 4-nitrotoluene-2-sulphonic acid is $\geq 98\%$ of theory (relative to reacted 4-nitrotoluene).

4-Nitrotoluene-2-sulphonic acid can be precipitated as crystals from the aqueous crude solution of 4-nitrotoluene-2-sulphonic acid, if appropriate after filtration and/or phase separation, by concentration and/or cooling and/or by establishing a suitable concentration of $(H_3O)^+$ ions, and the crystals are isolated.

A pure solution is preferably prepared from the crude solution of 4-nitrotoluene-2-sulphonic acid, if appropriate after filtering off the undissolved sulphone, by extracting the suspension or solution with a suitable solvent, if appropriate after separating off excess 4-nitrotoluene and if appropriate at elevated temperature.

Possible solvents for the extraction are organic solvents which are not miscible with water in all proportions, for example chlorinated aliphatic hydrocarbons with 1 to 5 carbon atoms, preferably 1 to 3 carbon atoms, such as methylene chloride, chloroform, carbon tetrachloride and dichloroethane, and/or aromatic hydrocarbons with 6 to 18 carbon atoms, preferably 6 to 12 carbon atoms, such as chlorobenzene, dichlorobenzene, benzene, toluene, o-, m- or p-xylene, ethylbenzene, cumene, tetralin, chloronaphthalene and methylnaphthalene.

Methylene chloride and/or alkylbenzenes, in particular toluene, are preferably used as solvents for the extraction.

The extraction of the crude solution with the organic solvent is carried out once or several times in a part by weight ratio of organic solvent to crude solution of about 1:25 to about 2:1, preferably in a ratio of 1:10 to 1:20.

After the last extraction, the residual amount of organic solvent dissolved in the aqueous phase is removed, if necessary, by incipient distillation.

An approximately 20 to 70% strength aqueous 4-nitrotoluene-2-sulphonic acid solution with the high purity desired is usually produced in this manner. The concentration of free sulphuric acid in the 4-nitrotoluene-2-sulphonic acid solution is generally less than 10 mol %, and is preferably about 3 to 7 mol % (relative to 4-nitrotoluene-2-sulphonic acid).

The extraction can be carried out discontinuously or continuously.

For example, the process according to the invention can be carried out by employing 0.7 to 1.3 mols of $SO_3$ per 1 mol of 4-nitrotoluene and interrupting the reaction by adding water when a conversion of at least about 85% of the reaction component not employed in excess has been reached. The unreacted 4-nitrotoluene optionally separated off from the aqueous solution by phase separation and/or recovered, for example by extraction, can be used again in the sulphonation.

In another embodiment of the process according to the invention, $SO_3$ is employed in an excess of up to 20%, preferably up to 15%, relative to the 4-nitrotoluene employed, and the reaction mixture is treated with water when an almost quantitative conversion of 4-nitrotoluene has been achieved. The residual amounts of 4-nitrotoluene are separated off, for example by extraction, if appropriate after filtering off the 5,5'-dinitro-2,2'-ditolyl sulphone formed as a by-product.

In a preferred embodiment of the process according to the invention, $SO_3$ and 4-nitrotoluene are employed in a molar ratio of 0.9:1 to 1.2:1, and the reaction is interrupted by adding water when the component not employed in excess has reacted to the extent of more than 90%. After hydrolysis of the sulphonation mixture, the unreacted 4-nitrotoluene can be recycled into the reaction, if appropriate after separating off the 5,5'-dinitro-2,2'-ditolyl sulphone formed in the course of the reaction. The sulphone can be separated off, for example, by filtration, or by distillation of the 4-nitrotoluene.

The process according to the invention can be carried out discontinuously or continuously. A stirred kettle, for example, can be used in the case of a discontinuous procedure.

In the case of a continuous procedure, the reaction can be carried out, for example, in a cascade of stirred kettles, in a reaction tube, in a thin film reactor or in a loop reactor, if necessary with finishing reactors.

The reaction can be carried out under an inert gas, but this is not essential for the process according to the invention.

According to the invention, gaseous $SO_3$ is preferably employed and reacted in an undiluted form and, for example, under normal pressure. Contamination of technical grade $SO_3$ by $SO_2$ does not have an adverse effect on the process according to the invention. A certain dilution of the gaseous $SO_3$ by an inert gas of, for example, up to 50% is possible, but provides no advantage with respect to the quality of the product and the procedure for the process and entails additional expense.

The gaseous $SO_3$ can be passed over the reaction mixture or, preferably, passed into the reaction mixture.

In a preferred embodiment, the process according to the invention is carried out continuously, for example by passing gaseous, undiluted $SO_3$ into a reactor at the same time as molten 4-nitrotoluene, through a feed system in the reaction mixture, and transferring the reaction mixture into a delay system, such as, for example, a cascade of stirred kettles. The hot sulphonation mixture flows from the main reactor, or if appropriate from the delay system, into a hydrolysis apparatus, for example, a stirred apparatus to which the amount of water necessary for hydrolysis and preparation of the 4-nitrotoluene-2-sulphonic acid solution of the desired concentration is simultaneously fed continuously.

The crude hydrolysis solution or the mixture passes, if appropriate, through an overflow into a delay system, such as, for example, another stirred kettle, from where it is fed into an extraction apparatus, if appropriate after separating off undissolved 4-nitrotoluene and 5,5'-dinitro-2,2'-ditolyl sulphone.

In another embodiment, the sulphone can be separated off by filtration before the extraction. Extraction is effected, for example, by feeding in toluene in counter-current at about 30° to 70° C. in a weight ratio of crude solution:toluene of about 10:1 to about 20:1.

After separating off the organic phase, the organic solvent can be redistilled, and fed again into the extraction apparatus. If appropriate, the 4-nitrotoluene separated off and/or extracted is redistilled and recycled into the main reactor. The sulphone can be obtained in crystalline form from the bottom product of the distillation and can be put to another use.

The 4-nitrotoluene-2-sulphonic acid solution prepared by the process according to the invention can be used for the preparation of very pure, crystalline 4-nitrotoluene-2-sulphonic acid.

Furthermore, 4-nitrotoluene-2-sulphonic acid can be used for the preparation of 4,4'-dinitrostilbene-2,2'-disulphonic acid, in which, for example, an approximately 30 to 50% strength aqueous solution of 4-nitrotoluene-2-sulphonic acid is reacted with oxidizing agents, for example with atmospheric oxygen. 4,4'-Dinitrostilbene-2,2'-disulphonic acid can be further processed by reduction to give 4,4'-diaminostilbene-2,2'-disulphonic acid (see Ber. 30, 3,100), and is an important intermediate product for the preparation of optical brighteners (A. Dorlars, C.-W. Schellhammer and J. Schroeder, Angew. Chem. 87, 693 (1975)).

A particularly high quality is required of the aqueous solution of 4-nitrotoluene-2-sulphonic acid in the reaction of this compound to give 4,4'-dinitrostilbene-2,2'-disulphonic acid (compare German Offenlegungsschrift No. 2,419,455). As described above, there are no problems in achieving the required quality by the process according to the invention.

The examples below are intended to illustrate the process according to the invention in more detail, but without restricting it to these examples.

EXAMPLE 1

75.6 g (0.94 mol) of gaseous sulphur trioxide are passed into a melt, warmed to 100° C., of 137 g (1 mol) of p-nitrotoluene in the course of 40 minutes. The melt is kept at 100° C., by cooling, during the introduction, and crystals separate out about 30 minutes after the start of the introduction. The melt is stirred at the same temperature for 1 hour. Analysis of a sample by hydrolysis in water (30 minutes, 90° C.) indicates that the reaction mixture (212.6 g) contains the following compounds: 91.3% of p-nitrotoluene-2-sulphonic acid, 6.5% of p-nitrotoluene and 2.1% of sulphuric acid, that is to say 94.6% of the sulphur trioxide has reacted to give p-nitrotoluenesulphonic acid.

EXAMPLE 2

296 g/hour of gaseous $SO_3$ and 533.3 g/hour of liquid 4-nitrotoluene are simultaneously metered continuously, through feed tubes, into a 0.3 l stirred apparatus in which the internal temperature is kept at 110° C. The thoroughly mixed, mobile sulphonation composition flows through an overflow into a 2 l stirred apparatus, which is also temperature-controlled at 110° C. The sulphonation composition flows from this delay vessel through an overflow into a 3 l stirred flask, into which about 1,450 g/hour of water are simultaneously fed; the temperature is adjusted to 95° C. The crude solution of 4-nitrotoluene-2-sulphonic acid passes through an overflow and, after filtration, into a storage tank.

Extraction (5 times with 150 ml of toluene each time) and incipient distillation to remove the residual toluene gives about 2,220 g/hour of a pure solution of 4-nitrotoluene-2-sulphonic acid (Gardner Colour Standard: colour number 6) having the following composition: 758.7 g of 4-nitrotoluene-2-sulphonic acid and 22.8 g of $H_2SO_4$, the sum of all the organic impurities being $\leq 5$ mg.

EXAMPLE 3

325 g/hour of gaseous $SO_3$ and 533 g/hour of 4-nitrotoluene are fed, at 120° C., into the same apparatus as that described under Example 2. The delay vessel is likewise kept at 120° C. Hydrolysis is effected at 95° C. with about 1,560 ml/hour of $H_2O$. After filtering off the sulphone (6.7 g/hour), extracting the crude solution (5 times with about 200 ml of toluene each time) at 60° C. and distilling off the residual toluene, 2,360 g/hour of a pure solution of 4-nitrotoluene-2-sulphonic acid having the following composition are obtained: 816.2 g of 4-nitrotoluene-2-sulphonic acid and 27.5 g of $H_2SO_4$, the sum of all the organic impurities being $\leq 5$ mg. Colour number 6 (Gardner Colour Standard).

What is claimed is:

1. In a process for the preparation of 4-nitrotoluene-2-sulphonic acid by reacting 4-nitrotoluene with gaseous sulphur trioxide at an elevated temperature, the improvement wherein molten 4-nitrotoluene is reacted with undiluted gaseous sulphur trioxide or gaseous technical grade $SO_3$ and diluted up to 50% by volume at a temperature in the range from 60° to 150° C. under a pressure above the vapor pressure of 4-nitrotoluene, in a molar ratio of sulphur trioxide to 4-nitrotoluene of 0.1:1 to 1.5:1, said sulphur trioxide being introduced into said molten 4-nitrotoluene and, after a conversion of at least 70 percent of the reaction component not employed in excess is achieved, the sulphonation mixture is treated with water.

2. Process according to claim 1 wherein the sulphonation mixture treated with water is subjected to a purification process.

3. Process according to claim 2 wherein the reaction mixture is purified by extraction with an organic solvent which is not miscible with water in all proportions.

4. Process according to claim 3 wherein a chlorinated aliphatic hydrocarbon with 1 to 5 carbon atoms is used as the organic solvent.

5. Process according to claim 3 wherein an aromatic hydrocarbon with 6 to 18 carbon atoms is used as the organic solvent.

6. Process according to claim 3 wherein methylene chloride and/or toluene is used as the organic solvent.

7. Process according to claim 1 wherein unreacted 4-nitrotoluene is recycled into the sulphonation stage.

8. Process according to claim 1 wherein $SO_3$ is employed in an excess of up to 20 percent, relative to 4-nitrotoluene employed.

9. Process according to claim 1 wherein the process is carried out continuously.

10. A process according to claim 1, wherein the gaseous $SO_3$ is undiluted or diluted up to 50%.

11. A process according to claim 1, wherein said gaseous sulphur trioxide is technical grade $SO_3$.

* * * * *